US008866107B2

(12) United States Patent
Cui

(10) Patent No.: US 8,866,107 B2
(45) Date of Patent: Oct. 21, 2014

(54) WAVEFRONT COMPENSATION FOR DEEP TISSUE OPTICAL MICROSCOPY

(75) Inventor: Meng Cui, Ashburn, VA (US)

(73) Assignee: Howard Hughes Medical Institute, Chevy Chase, MD (US)

(*) Notice: Subject to any disclaimer, the term of this patent is extended or adjusted under 35 U.S.C. 154(b) by 263 days.

(21) Appl. No.: 13/548,011

(22) Filed: Jul. 12, 2012

(65) Prior Publication Data

US 2013/0182253 A1    Jul. 18, 2013

Related U.S. Application Data

(63) Continuation-in-part of application No. 13/353,029, filed on Jan. 18, 2012, now Pat. No. 8,716,677.

(60) Provisional application No. 61/506,886, filed on Jul. 12, 2011, provisional application No. 61/434,204, filed on Jan. 19, 2011.

(51) Int. Cl.
| | | |
|---|---|---|
| *G01J 1/58* | (2006.01) | |
| *G02B 26/06* | (2006.01) | |
| *G01J 9/02* | (2006.01) | |
| *G01N 21/64* | (2006.01) | |
| *G01J 9/04* | (2006.01) | |
| *G01N 21/49* | (2006.01) | |
| *G02B 21/00* | (2006.01) | |

(52) U.S. Cl.
CPC ............... *G01N 21/49* (2013.01); *G02B 26/06* (2013.01); *G01J 9/02* (2013.01); *G02B 21/0072* (2013.01); *G01N 21/64* (2013.01); *G01J 9/04* (2013.01); *G02B 21/0004* (2013.01)
USPC ..................................... 250/459.1; 250/252.1

(58) Field of Classification Search
CPC ............................... G01J 9/00; G01B 9/02091
USPC ............................................ 250/459.1, 252.1
See application file for complete search history.

(56) References Cited

U.S. PATENT DOCUMENTS 6,185,446 B1 *   2/2001   Carlsen, Jr. ................... 600/411
6,483,641 B1    11/2002   MacAulay
(Continued)

OTHER PUBLICATIONS

M. Cui, "Parallel wavefront optimization method for focusing light through random scattering media," Opt. Lett. vol. 36, No. 6, 870-872 (Mar. 15, 2011).

(Continued)

*Primary Examiner* — David Porta
*Assistant Examiner* — Abra Fein
(74) *Attorney, Agent, or Firm* — DiBerardino McGovern IP Group LLC

(57) ABSTRACT

Wavefront distortions of an optical beam are measured. The transverse optical modes of the optical beam are partitioned into a plurality of subsets of transverse optical modes, one of the subsets of transverse optical modes is selected as the current subset, and the optical beam is modulated based on the current subset by maintaining the transverse optical modes of the optical beam that are outside the current subset stable, and modulating the transverse optical modes of the optical beam within the current subset. A non-linear optical signal is generated from the modulated optical beam by directing the modulated optical beam through a non-linear optical system that includes a random scattering medium, the power of the generated non-linear optical signal is measured, and, based on the measured power, values of the spatial phase for the optical beam at transverse optical modes are extracted within the current subset.

22 Claims, 11 Drawing Sheets

(56) References Cited

U.S. PATENT DOCUMENTS

| | | | |
|---|---|---|---|
| 6,556,854 | B1 | 4/2003 | Sato et al. |
| 6,699,189 | B1 * | 3/2004 | Lin et al. .................. 600/437 |
| 6,741,346 | B1 | 5/2004 | Gerstner et al. |
| 6,771,417 | B1 | 8/2004 | Wolleschensky et al. |
| 6,995,810 | B2 | 2/2006 | Melton |
| 7,423,745 | B2 | 9/2008 | Moribe et al. |
| 7,456,378 | B2 | 11/2008 | Sasaki et al. |
| 7,460,248 | B2 | 12/2008 | Kurtz et al. |
| 7,633,053 | B2 | 12/2009 | Wolleschensky et al. |
| 7,733,564 | B2 | 6/2010 | Wolleschensky et al. |
| 2001/0030740 | A1 | 10/2001 | Mori et al. |
| 2002/0109078 | A1 | 8/2002 | Housh et al. |
| 2003/0035200 | A1 * | 2/2003 | Aoki et al. .................. 359/308 |
| 2003/0062464 | A1 | 4/2003 | Byren et al. |
| 2004/0189999 | A1 | 9/2004 | De Groot et al. |
| 2005/0187722 | A1 | 8/2005 | Bechhoefer |
| 2007/0012871 | A1 | 1/2007 | Wagner et al. |
| 2007/0086919 | A1 | 4/2007 | Akcakir |
| 2007/0121201 | A1 | 5/2007 | Sander |
| 2007/0188856 | A1 | 8/2007 | MacAulay |
| 2008/0316571 | A1 | 12/2008 | MacAulay |
| 2009/0028198 | A1 | 1/2009 | Belenkii |
| 2009/0137990 | A1 | 5/2009 | Sheinis |
| 2011/0006231 | A1 | 1/2011 | Betzig et al. |

OTHER PUBLICATIONS

W.B. Bridges, et al., "Coherent optical adaptive techniques," Appl. Optics vol. 13, No. 2, 291-300 (Feb. 1974).

Jan Huisken, et al., "Optical Sectioning Deep Inside Live Embryos by Selective Plane Illumination Microscopy," Science 305, 1007-1009 (2004).

Eric Betzig, et al., "Imaging Intracellular Fluorescent Proteins at Nanometer Resolution," Science 313, 1642-1645, Sep. 15, 2006.

Brian A.Wilt, et al., "Advances in Light Microscopy for Neuroscience," Annu. Rev. Neurosci. 32, 435-506 (2009).

Winfried Denk, et al., "Two-Photon Laser Scanning Fluorescence Microscopy," Science 248, 73-76, Apr. 1990.

David Huang, et al., "Optical Coherence Tomography," Science 254, 1178-1181 (1991).

I.M. Vellekoop, et al., "Focusing coherent light through opaque strongly scattering media," Opt. Lett. vol. 32, No. 16, 2309-2311 (Aug. 15, 2007).

Ivo M. Vellekoop and Christof M. Aegerter "Scattered light fluorescence microscopy: imaging through turbid layers." Optics Letters vol. 35, No. 8: 1245-1247 (Apr. 15, 2010).

Fritjof Helmchen and Winifried Denk, "Deep tissue two-photon microscopy," Nature Methods, vol. 2, No. 12, Dec. 2005, pp. 932-940, 235.

Thomas Bifano et al., "Micromachined Deformable Mirrors for Adaptive Optics," Proceedings of SPIE vol. 4825 (2002), pp. 10-13.

Delphine Debarre et al., "Image-based adaptive optics for two-photon microscopy," Aug. 15, 2009, vol. 34, No. 16, Optics Letters, pp. 2495-2497.

A. Leray et al., "Enhanced Background Rejection in Thick Tissue with Differential-Aberration Two-Photon Microscopy," Biophysical Journal, vol. 94, Feb. 2008, pp. 1449-1458.

M. Schwertner et al., "Measurement of specimen-induced aberrations of biological samples using phase stepping interferometry," J. of Microscopy, vol. 213, Jan. 2004, pp. 11-19.

I.M. Vellekoop et al., "Phase control algorithms for focusing light through turbid media," Optics Comm. 281 (2008) 3071-3080.

Martin J. Booth, "Adaptive optics in microscopy," Phil. Trans. R. Soc. A (2007) 365, 2829-2843, published Sep. 13, 2007.

Nanguang Chen et al., "Focal modulation microscopy," Nov. 10, 2008, vol. 16, No. 23, Optics Express 18764.

Yaopeng Zhou et al., "Adaptive optics two-photon fluorescence microscopy," Proc. of SPIE vol. 6467, 646705 (2007).

M. Chalfie, Y. Tu, G. Euskirchen, W. W. Ward, D. C. Prasher, Green fluorescent protein as a marker for gene-expression. Science 263, 802 (Feb. 1994).

C. Xu, et al., Multiphoton fluorescence excitation: New spectral windows for biological nonlinear microscopy. Proc. of the Nat. Aca. of Sci. in the USA 93, 10763 (Oct. 1996).

Meng Cui and Changhuei Yang, "Implementation of a digital optical phase conjugation system and its application to study the robustness of turbidity suppression by phase conjugation," Optics Express, Feb. 15, 2010, vol. 18, No. 4, pp. 3444-3455.

Biru Wang and Martin J. Booth, "Optimum deformable mirror modes for sensorless adaptive optics," Optics Communications 282 (2009) pp. 4467-4474.

Na Ji, et al., "Advances in the speed and resolution of light microscopy," Current Opinion in Neurobiology 2008, 18:605-616.

Gaddum Duemani Reddy and Peter Saggau, "Fast three-dimensional laser scanning scheme using acouto-optic deflectors," Journal of Biomedical Optics 10(6), 064038 (Nov./Dec. 2005), pp. 1-10.

W. R. Zipfel, R. M. Williams, W. W. Webb, Nonlinear magic: Multiphoton microscopy in the biosciences. Nature Biotechnology 21, 1368 (Nov. 2003).

C. W. Freudiger et al., Label-free biomedical imaging with high sensitivity by stimulated raman scattering microscopy. Science 322, 1857 (Dec. 2008).

R. Y. Tsien, The green fluorescent protein. Annual Review of Biochemistry 67, 509 (1998).

T. A. Planchon et al., Rapid three-dimensional isotropic imaging of living cells using bessel beam plane illumination. Nature Methods 8, 417 (May 2011).

V. Ntziachristos, J. Ripoll, L. H. V. Wang, R. Weissleder, Looking and listening to light: The evolution of whole-body photonic imaging. Nature Biotechnology 23, 313 (2005).

X. D. Wang et al., Noninvasive laser-induced photoacoustic tomography for structural and functional in vivo imaging of the brain. Nature Biotechnology 21, 803 (Jul. 2003).

P. Theer, M. T. Hasan, W. Denk, Two-photon imaging to a depth of 1000 mu m in living brains by use of a ti : Al2o3 regenerative amplifier. Optics Letters 28, 1022 (Jun. 2003).

D. P. M. Gower, Optical phase conjugation. (Springer-Verlag, New York, 1994).

J. W. Hardy, Adaptive optics for astronomical telescopes. (Oxford, 1998).

M. Cui, A high speed wavefront determination method based on spatial frequency modulations for focusing light through random scattering media. Opt. Ex. 19, 2989 (Feb. 2011).

O. Katz, E. Small, Y. Bromberg, Y. Silberberg, Focusing and compression of ultrashort pulses through scattering media. Nature Photonics 5, 372 (Jun. 2011).

C. L. Hsieh, et al., Imaging through turbid layers by scanning the phase conjugated second harmonic radiation from a nanoparticle. Optics Express 18, 20723 (2010).

G. Yang, et al., Thinned-skull cranial window technique for long-term imaging of the cortex in live mice. Nature Protocols 5, 201 (2010).

Boston Micromachines Corporation Shaping Light, Specification Sheet for Kilo-DM available at www.bostonmicromachines.com, May 2011, 1 page.

Wikipedia article, "Adaptive Optics," en.wikipedia.org/wiki/Adaptive_optics, prior to Jul. 12, 2012, 7 pages.

Wikipedia article, "Nonlinear optics," en.wikipedia.org/wiki/Optical_phase_conjugation#cite_note-7, prior to Jul. 12, 2012, 11 pages.

* cited by examiner

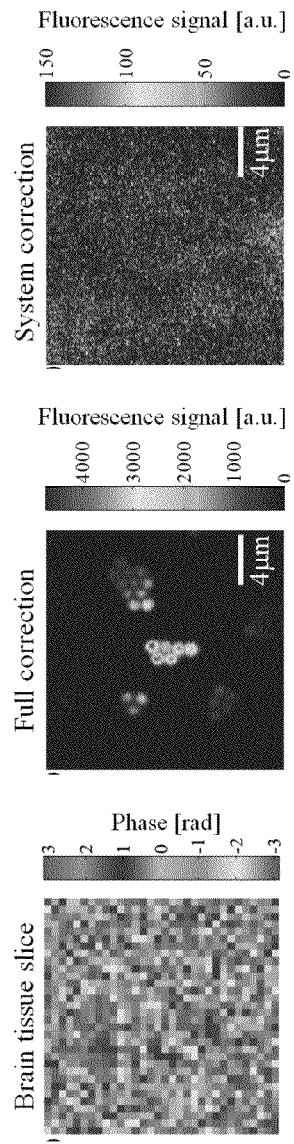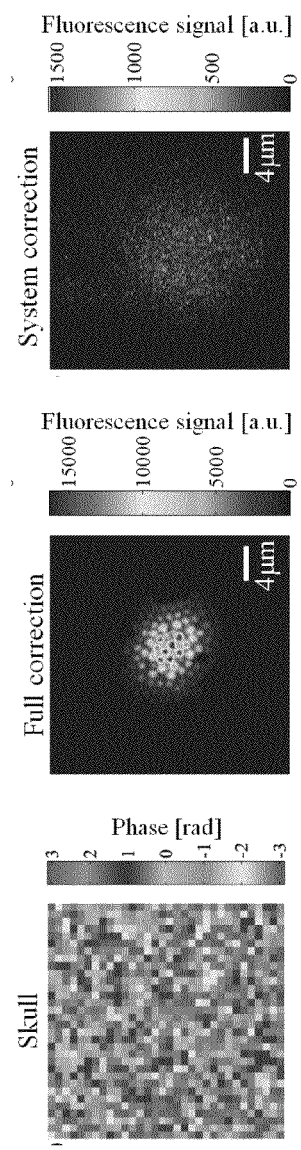

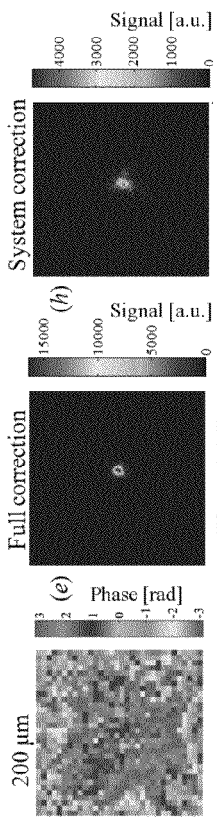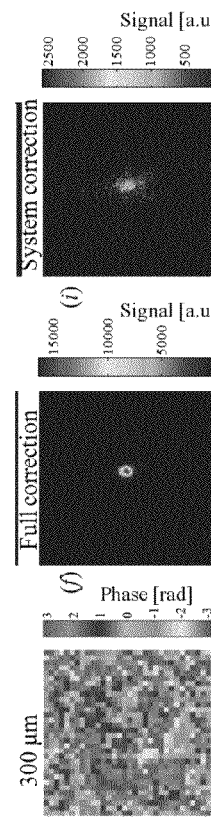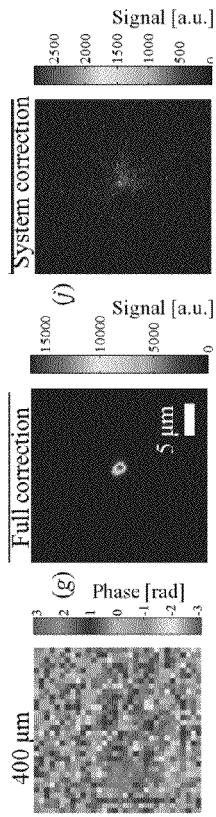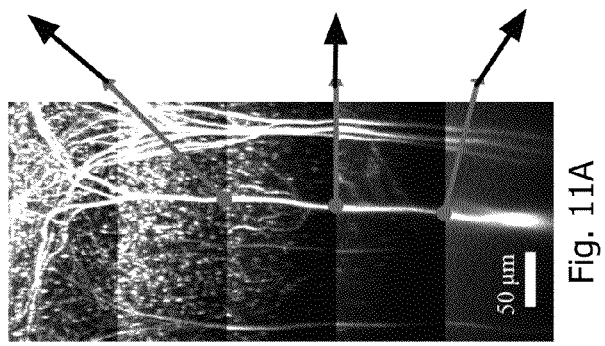

WAVEFRONT COMPENSATION FOR DEEP TISSUE OPTICAL MICROSCOPY

CROSS-REFERENCE TO RELATED APPLICATION

This application claims priority to U.S. Application No. 61/506,886, filed on Jul. 12, 2011 and entitled "Iterative multiphoton adaptive compensation technique for deep tissue optical microscopy." This application is a continuation-in-part of U.S. application Ser. No. 13/353,029, filed Jan. 18, 2012, which claimed priority to U.S. Application No. 61/434,204, filed. Jan. 19, 2011. All of these applications are incorporated herein by reference in their entirety.

TECHNICAL FIELD

The disclosed subject matter relates to a method and system for compensating for wavefront aberrations and distortion using nonlinearity of multiphoton microscopy signals and iterative feedback.

BACKGROUND

When an optical beam from a light source such as a laser passes through a scattering medium such as biological tissue, random elastic scattering within the biological tissue and optical aberration in the microscope objective can distort and move the optical beam wavefront and any image of the optical beam on a target, thus limiting the achievable imaging depth. Images produced by the optical beam are blurred by these distortions. The wavefront of the optical beam can be considered a surface passing through all points and having the same phase; the wavefront is generally perpendicular to the direction of propagation of the optical beam. The direction of propagation of the optical beam is also referred to as its optic axis.

One technique called adaptive optics has been developed to compensate for these distortions. In traditional adaptive optics, a wavefront sensor can be used to detect the wavefront of the optical beam, and a computer receives the output from the wavefront sensor and corrects for the distortions by reshaping a deformable mirror that lies in the path of the optical beam.

SUMMARY

In one general aspect, a method for measuring wavefront distortions of an optical beam directed inside a random scattering medium is performed. The method includes partitioning the transverse optical modes of the optical beam into a plurality of subsets of transverse optical modes, selecting one of the subsets of transverse optical modes as the current subset, and modulating the optical beam based on the current subset by maintaining the transverse optical modes of the optical beam that are outside the current subset stable, and modulating the transverse optical modes of the optical beam within the current subset. The method also includes generating a non-linear optical signal from the modulated optical beam by directing the modulated optical beam through a non-linear optical system that includes the random scattering medium, measuring the power of the generated non-linear optical signal, and, based on the measured power, extracting values of the spatial phase for the optical beam at transverse optical modes within the current subset, the values extracted being those that reduce the wavefront distortions in the optical beam.

Implementations can include one or more of the following features. For example, the method also can include setting the spatial phase for the optical beam at transverse optical modes within the current subset based on the extracted values of the spatial phase that reduce the wavefront distortions in the optical beam. The method also can include, after setting the spatial phase for the optical beam at optical modes within the current subset, determining if any of the optical modes of the partition have not yet been selected as the current subset. If a particular subset of transverse optical modes from the partition has not yet been selected as the current subset, then the particular subset of transverse optical modes can be selected as the current subset, the optical beam can be modulated based on the current subset, the non-linear optical signal can be generated from the modulated optical beam by directing the modulated optical beam through the non-linear optical system, the power of the generated non-linear optical signal can be measured, and, based on the measured power, values of the spatial phase for the optical beam at optical modes within the current subset can be extracted, the values extracted being those that reduce the wavefront distortion in the optical beam.

The method can also include setting the spatial phase for the optical beam at optical modes within the current subset based on the extracted vales of the spatial phase that reduce the wavefront distortion in the optical beam. In some implementations, whether the wavefront distortion has been reduced to within an acceptable range is determined. The wavefront distortion can be considered to be reduced to within the acceptable range if the optical beam forms a diffraction-limited focus inside the random scattering medium without the need for a point guide star. Once it is determined that the wavefront distortion has been reduced to within an acceptable range, all of the optical modes of the optical beam may be caused to be constant, the optical beam can be scanned along a transverse plane as the optical beam travels inside the random scattering medium, and the random scattering medium can be imaged.

Directing the modulated optical beam through the non-linear optical system can include directing the modulated optical beam through the random scattering medium. Generating the non-linear optical signal can include generating a second harmonic generation of the modulated optical beam by passing the modulated optical beam through the random scattering medium, and measuring the power of the generated non-linear optical signal can include measuring the power of the second harmonic generation. Directing the modulated optical beam through the non-linear optical system can include directing the modulated optical beam through a multi-photon fluorescence microscope toward a biological sample. Generating the non-linear optical signal from the modulated optical beam can include generating multi-photon fluorescence from the biological sample due to a multi-photon interaction of the modulated optical beam with the biological sample, and measuring the power of the generated non-linear optical signal can include measuring the power of the multi-photon fluorescence.

In some implementations, measuring the power of the generated non-linear optical signal includes Fourier transforming the measured power, and extracting values of the spatial phase for the optical beam at optical modes within the current subset can include extracting the values of the spatial phase from the Fourier transformed data. Extracting the values can include extracting the values without analyzing the spectrum of the generated non-linear optical signal. Modulating the optical modes of the optical beam within the current subset can include modulating each optical mode within the current subset at a distinct frequency. Partitioning the optical modes into a plurality of subsets of transverse optical modes can include partitioning the transverse optical modes into at least three subsets of transverse optical modes.

In another general aspect, an apparatus for measuring wavefront distortions of an optical beam directed inside a random scattering medium includes a wavefront correction device having a spatial phase profile on its surface and configured to receive the optical beam, and output a modulated optical beam. The apparatus also includes a non-linear optical system that receives the modulated optical beam output from the wavefront correction device and is configured to generate a non-linear optical signal from the modulated optical beam, a power detector configured to detect a power of the generated non-linear optical signal, and a control system connected to the wavefront correction device and to the power detector. The control system is configured to partition the transverse optical modes of the optical beam into a plurality of subsets of transverse optical modes, select a transverse optical mode subset from the partition as the current subset, output a signal to the wavefront correction device to cause it to modulate the optical beam by modulating the transverse optical modes of the optical beam within the current subset and by keeping the transverse optical modes of the optical beam outside the current subset constant, receive the detected power from the power detector, and based on the measured power, extract values of the spatial phase for the optical beam at transverse optical modes within the current subset, the values extracted being those that reduce the wavefront distortions in the optical beam.

Implementations can include one or more of the following features. The control system can be configured to set the spatial phase for the optical beam at transverse optical modes within the current subset based on the extracted values of the spatial phase that reduce the wavefront distortions in the optical beam. The apparatus can also include an objective that directs the optical beam toward and into the random scattering medium. The generated non-linear optical signal can include the second harmonic generation signal generated from the interaction of the optical beam with the random scattering medium. The non-linear optical system can include a multi-photon fluorescence microscope and the random scattering medium can include a biological tissue sample. The generated non-linear optical signal includes the multi-photon fluorescence output from the biological tissue sample due to a multi-photon interaction of the modulated optical beam with the biological tissue sample.

In another general aspect, a method for measuring wavefront distortions of an optical beam directed inside a random scattering medium includes partitioning the transverse optical modes of the optical beam into a plurality of subsets of transverse optical modes. The method also includes, for each transverse optical mode subset of the partition: (A) selecting one of the transverse optical mode subsets as the current subset, (B) modulating the optical beam based on the current subset by maintaining the transverse optical modes of the optical beam that are outside the current subset constant and modulating the transverse optical modes of the optical beam within the current subset, (C) generating a non-linear optical signal from the modulated optical beam by directing the modulated optical beam through a non-linear optical system that includes the random scattering medium, (D) measuring the power of the generated non-linear optical signal, (E) based on the measured power, extracting values of the spatial phase for the optical beam at transverse optical modes within the current subset, the values extracted being those that reduce the wavefront distortions in the optical beam, (F) setting the spatial phase for the optical beam at transverse optical modes within the current subset based on the extracted values of the spatial phase that reduce the wavefront distortions in the optical beam, and repeating steps A-F until the wavefront distortions of the optical beam has been reduced to an acceptable amount.

Implementations of the techniques discussed above can include a method or process, a system or apparatus, a kit, or computer software stored on a computer-accessible medium. The details of one or more implementations are set forth in the accompanying drawings and the description below. Other features will be apparent from the description and drawings, and from the claims.

DESCRIPTION OF DRAWINGS

FIGS. 10A and 10D show exemplary compensation profiles;

FIGS. 10B and 10E show examples of two-photon fluorescence (TPF) imaging with full correction;

FIGS. 10C and 10F show examples of TPF imaging with system correction;

FIG. 11A shows an example of a maximum intensity projection;

FIGS. 11B-11D show exemplary compensation profiles determined at 200, 300, and 400 μm depth, respectively;

FIGS. 11E-11G show exemplary TPF images of dendrite with full correction;

FIGS. 11H-11J show exemplary TPF images of dendrite with system correction;

Like reference numbers refer to like elements.

DESCRIPTION

This description relates to an iterative wavefront compensation technique that takes advantage of the nonlinearity of multiphoton optical signals to determine and compensate for wavefront distortions such as optical aberrations and random scattering, and focus light inside deep tissues. The technique is tested with a variety of biological samples, including brain tissue, skull and lymph nodes. High quality three-dimensional imaging can be realized at depths beyond the reach of conventional multiphoton microscopy. Moreover, the required laser excitation power can be greatly reduced in deep tissues, deviating from the power requirement of ballistic light excitation.

Figure 1:
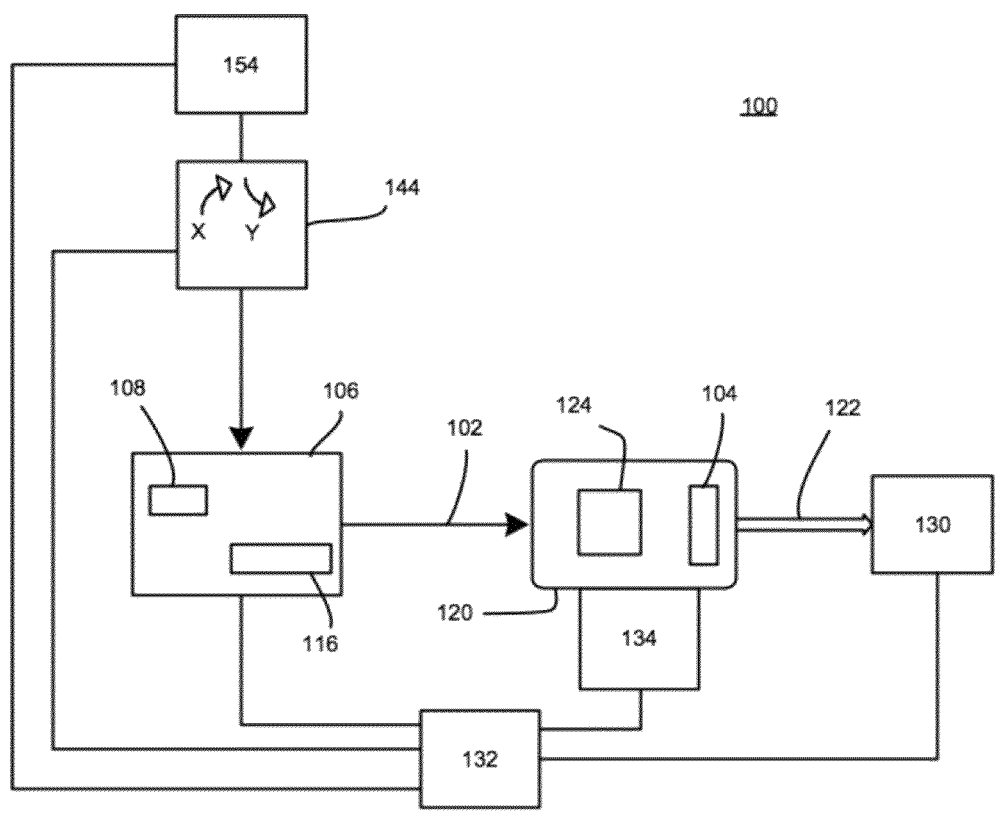
FIG. 1 is a block diagram of an iterative parallel wavefront phase modulation apparatus.

Referring to FIG. 1, an apparatus 100 is designed for measuring and compensating wavefront distortions of an optical beam 102 traveling inside a random scattering medium 104. The apparatus 100 includes a wavefront correction apparatus 106, a nonlinear optical system 120 defined, in part by the interaction of the optical beam with the random scattering medium 104, a power detector 130, and a control system 132.

Additionally, the apparatus 100 includes an imaging system 134 that is used in combination with a transverse scanning optical system 144 to image the random scattering medium 104 once the wavefront distortions of the optical beam 102 are measured and compensated.

The apparatus 100 performs an iterative procedure that uses the power of a nonlinear signal 122 produced from the nonlinear optical system 120 while the optical beam interacts with the random scattering medium 104 to quickly measure the spatial phase and reduce wavefront distortions in the optical beam 102. The spatial phase of the optical beam 102 is the phase term of the electric field at a particular point in the X, Y plane that is perpendicular to (transverse to) the propagation direction Z (or optic axis) of the optical beam 102. This procedure requires no spectrum analysis or measurement of the nonlinear signals. Moreover, this procedure is effective for either smooth or completely random distortions applied to the optical beam 102. Details about the procedure are provided below following a description of the components of the apparatus 100.

The optical beam 102 is produced from a light source 154, which includes, among other components, a coherent light source such as an oscillator or a laser, for example, a continuous wave laser or a pulsed laser.

The transverse scanning optical system 144 includes, among other possible features, a first set of optical elements such as an actuator that moves a respective mirror (not shown in FIG. 1) configured to scan the optical beam 102 along a first direction X that is transverse to the optic axis and a second set of optical elements such as an actuator that moves a respective mirror (not shown in FIG. 1) configured to scan the optical beam 102 along a second direction Y that is transverse to the optic axis. The transverse scanning optical system 144 performs the X, Y scanning during the imaging of the random scattering medium 104, as discussed below.

The wavefront correction apparatus 106 includes, among other features, a set of optical components 108 such as lenses, lens relays, and mirrors, for directing and shaping the optical beam, and a wavefront correction device 116. The wavefront correction device 116 can be any device that controls and modulates the wavefront of the optical beam 102. The device 116 can be reflective or transmissive, depending on the application.

The wavefront correction device 116 has a spatial phase profile on its surface and is configured to receive the optical beam 102, and output a modulated optical beam. In particular, the wavefront correction device 116 is a two-dimensional (2D) mirror array of phase elements that provide phase only modulation. Each element is configured to modulate an optical mode of the optical beam 102. During modulation, each phase element of the array that is modulated is dithered at a unique frequency. In implementations in which the wavefront correction device 116 is a reflective device, the optical beam 102 input to the device 116 is reflected from the surface of each of the phase elements, with at least some of the optical modes of the optical beam 102 being modulated.

An example of such a device is a micro-electromechanical system (MEMS) that can be a continuous deformable mirror or a segmented deformable mirror (which is sometimes referred to as a spatial light modulator or SLM). In some implementations, the wavefront correction device is the Kilo-DM produced by Boston Micromachines Corporation, which provides a 32×32 array of pixels for a total of 1,024 pixels, with each non-corner pixel having a respective actuator.

In other implementations, the wavefront correction device 116 can be an SLM produced by Boulder Nonlinear Systems of Lafayette, Colo., or from HOLOEYE Photonics AG of Berlin-Adlershof, Germany.

The power detector 130 is a device that detects the power of the nonlinear signal 122. Thus, for example, the power detector 130 can be a photo-multiplier tube (PMT) or a photodiode.

The non-linear optical system 120 receives the modulated optical beam output from the wavefront correction device 116 and is configured to generate the non-linear optical signal 122 from the modulated optical beam. The non-linear optical system 120, which includes the random scattering medium 104, is any system that interacts with the modulated optical beam in a non-linear manner. The non-linear response of the system 120 results in an intensity-dependent variation of the propagation characteristics of the non-linear signal 122 or it creates a non-linear signal 122 that propagates at a new frequency or direction. Thus, the non-linear optical system 120 can be a multi-photon fluorescence microscope that includes an objective 124 that directs the optical beam 102 toward the random scattering medium 104, which is a biological tissue sample. The nonlinear optical signal 122 produced by this interaction is a multi-photon fluorescence signal. As another example, the non-linear optical system 120 can be a second harmonic imaging microscope that includes the objective 124 that directs the optical beam 102 toward the random scattering medium 104, which is the biological tissue sample. The nonlinear signal 122 produced by this interaction is a second harmonic generation signal.

The non-linear optical signal 122 has a power (which is measured by the power detector 130) that is proportional to an input power of the optical beam 102 raised to an Nth power. The non-linear optical signal 122 is used in the apparatus 100 to perform wavefront correction because modulation imparted by the wavefront correction device 116 effects the interaction between the non-linear optical system 120 and the modulated optical beam 102, and this effect is observable in the non-linear optical signal 122 output from the system 120. To put it another way, the non-linear optical signal 122 has a strong dependence on the spatial phase of the optical beam 102 and therefore it is modulated because the phase modulation produced by the wavefront correction device 116 changes the wavefront of the optical beam 102.

The control system 132 receives data from the power detector 130 and the imaging system 134 and sends instructions to the wavefront correction apparatus 106, the transverse scanning optical system 144, the light source 154, and the imaging system 134 based on this received information, as discussed in greater detail below.

The control system 132 can include a programmable machine that is able to respond to instructions in a well-defined manner and can execute instructions such as found in a program or engine internal to or external to the control system 132. The control system 132 can include electronic and digital components, including hardware needed to implement the instructions and read and access data, such as an electronic processor. The control system 132 can also include a communication mechanism that is able to communicate with the power detector 130 and other components of the apparatus 100 or to an external network through one or more communication channels. The control system 132 can include internal memory that can store information about components of the apparatus 100.

The control system 132 can implement processes, which are described below, as executable computer program instructions stored on a computer-readable storage medium (which can be within the control system 132 or external to the control system 132). The computer-readable storage medium can be implemented as one or more types of computer-readable storage media including volatile or non-volatile memory, removable or non-removable memory, erasable or non-erasable memory, writeable or re-writeable memory, and so forth. The terms "computer-readable storage medium" and "computer-readable storage media" may or may not consist of propagating signals and other types of transitory computer-readable media.

Figure 2A:
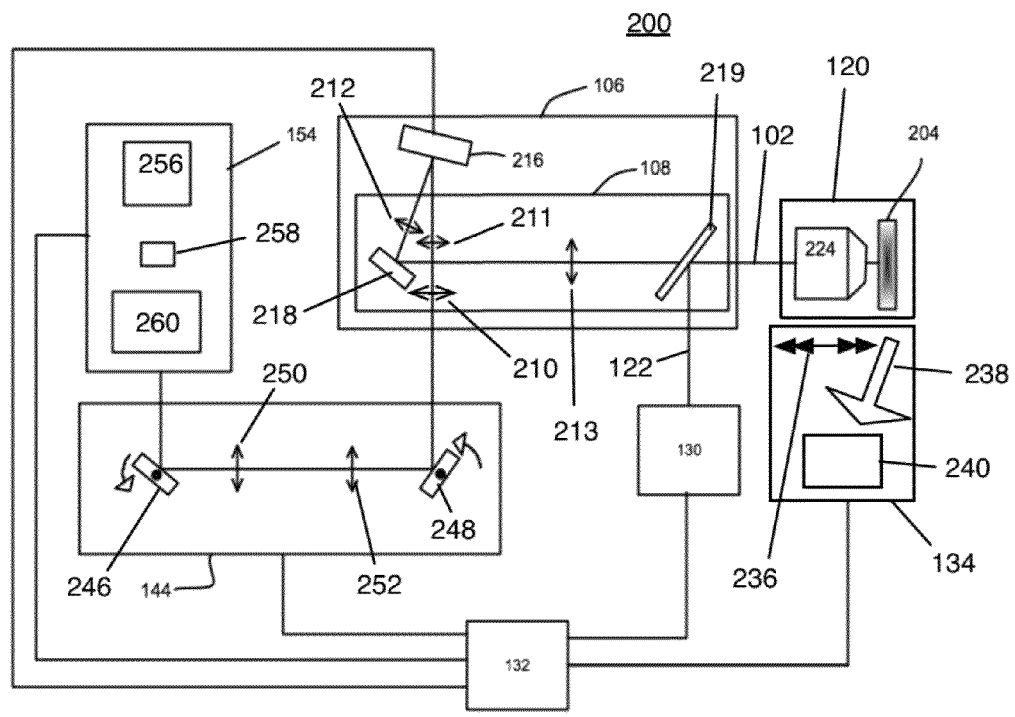
FIG. 2A is a block diagram of an exemplary iterative parallel wavefront phase modulation apparatus.

Referring to FIG. 2A, an exemplary apparatus 200 is shown. In this implementation, the light source 154 includes a tunable femtosecond oscillator laser 256, whose power is regulated by an electro-optic (EO) modulator 258. The light source 154 can also include other components such as a dispersion compensation system 260 that includes a prism pair compressor.

In this implementation, the transverse scanning optical system 144 includes an X scanning mirror 246 that scans or sweeps the optical beam 102 along the X direction under control of an actuator that is controlled by the control system 232, and a Y scanning mirror 248 that scans or sweeps the optical beam 102 along the Y direction under control of an actuator that is controlled by the control system 232. The X and Y directions are transverse to the Z direction (the optic axis) of the optical beam 102 and are transverse to each other. Additionally, the transverse scanning optical system 144 can include a relay lens pair 250, 252 that images the X scanning mirror 246 to the Y scanning mirror 248.

In this example, the wavefront correction apparatus 106 includes a wavefront correction device 216 that is a high-speed segmented deformable mirror based on MEMS technology, with a 32×32 array of segmented pixels having a 1.5 μm stroke. The wavefront correction apparatus also includes an exemplary set of optical components 108, including a set of relay lens pairs 210, 211 and 212, 213, a mirror 218, and a long-pass dichroic beam splitter 219.

The non-linear optical system 120 includes a microscope objective 224 that images the optical beam 102 onto a biological sample 204. In one implementation, the objective 224 is a NA 1.0 20× water immersion objective. The biological sample 204 is a random scattering medium that produces the non-linear optical signal 122, which is detected by the power detector 130 during the wavefront correction steps. This non-linear optical signal 122 can be, for example, a multi-photon fluorescence signal or a second harmonic generation signal. In this implementation, the non-linear optical signal 122 is collected by the objective 224 and directed by the beam splitter 219 onto the power detector 130, which can be a PMT.

Figure 2B:
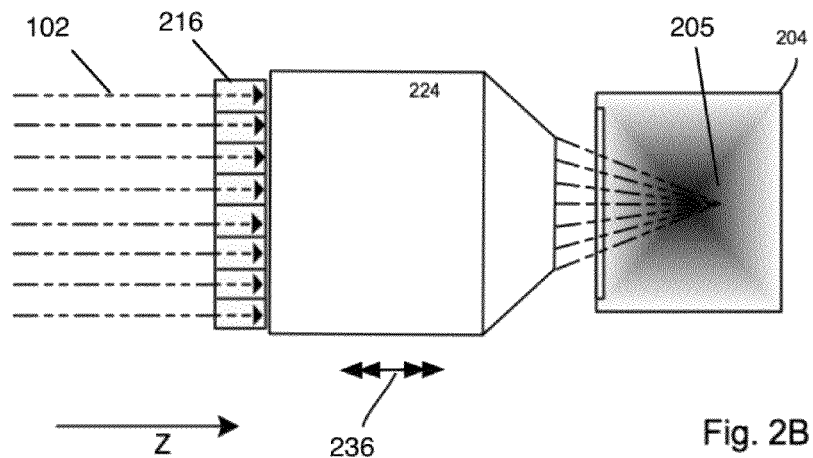
FIG. 2B is an expanded view of an exemplary nonlinear optical system including a microscope objective and a biological tissue sample within the exemplary iterative parallel wavefront phase modulation apparatus of FIG. 2A.

The apparatus 200 also includes the imaging system 134. As shown in more detail in FIG. 2B, the imaging system 134 includes an actuation system 236 that is coupled to the objective 224 to translate the objective 224 along the optic axis (or Z axis) of the optical beam 102. The imaging system 134 also includes an imaging detector 240 that captures the non-linear optical signal 238 produced during imaging. The imaging detector 240 and the actuation system 236 are connected to the control system 132.

Figure 3:
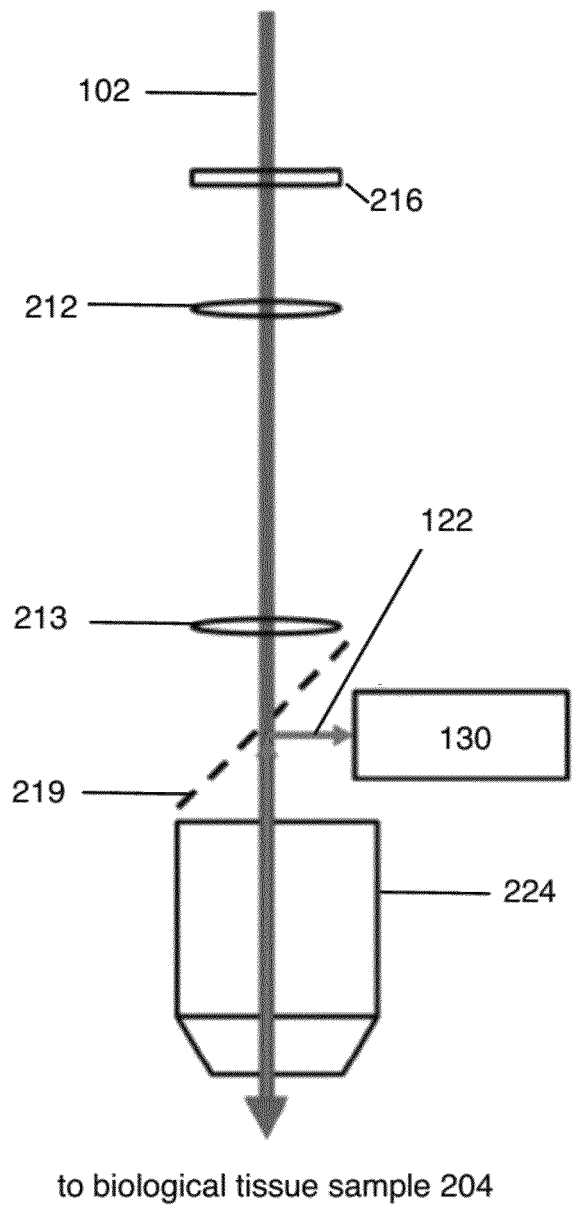
FIG. 3 is another view of the apparatus of FIG. 2A.

Referring to FIG. 3, only the basic elements of the exemplary apparatus 200 of FIG. 2A are shown. In the apparatus 200, the imaging signal 238 generated from the interaction of the optical beam 102 with the biological tissue sample 204 is used as the non-linear optical signal 122.

Figure 4:
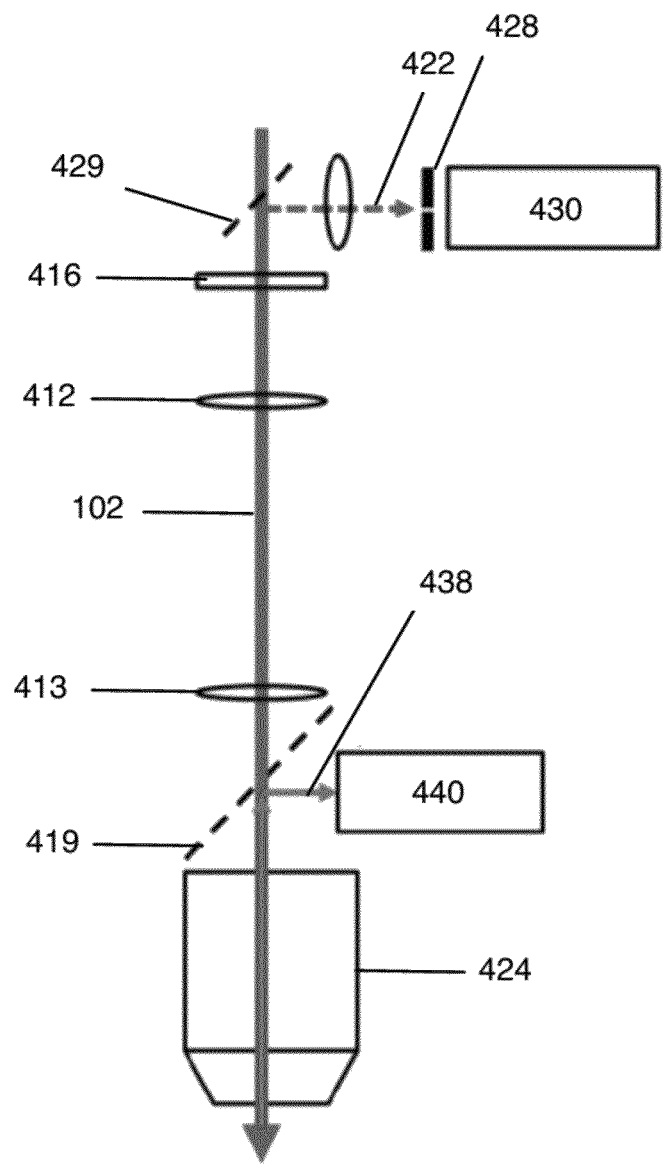
FIG. 4 shows an exemplary apparatus that includes a relay lens pair and a beam splitter.

A second scheme is shown in FIG. 4, which shows the basic elements of another exemplary apparatus 400 that includes the relay lens pair 412, 413 and the beam splitter 419 that image the optical beam 102 onto the objective 424. The apparatus 400 includes a confocal detection system that includes a pinhole 428 in front of the power detector 430. In this apparatus 400, backscattered ballistic light 422 from the focus within the biological tissue sample 204 is directed toward the confocal detection system using a beam splitter 429. Thus, the non-linear optical signal 122 that is detected in the apparatus 400 is the backscattered ballistic light 422 while the non-linear optical signal 438 that is used for imaging is another signal produced by the interaction of the optical beam 102 with the biological tissue sample 404.

Figure 5:
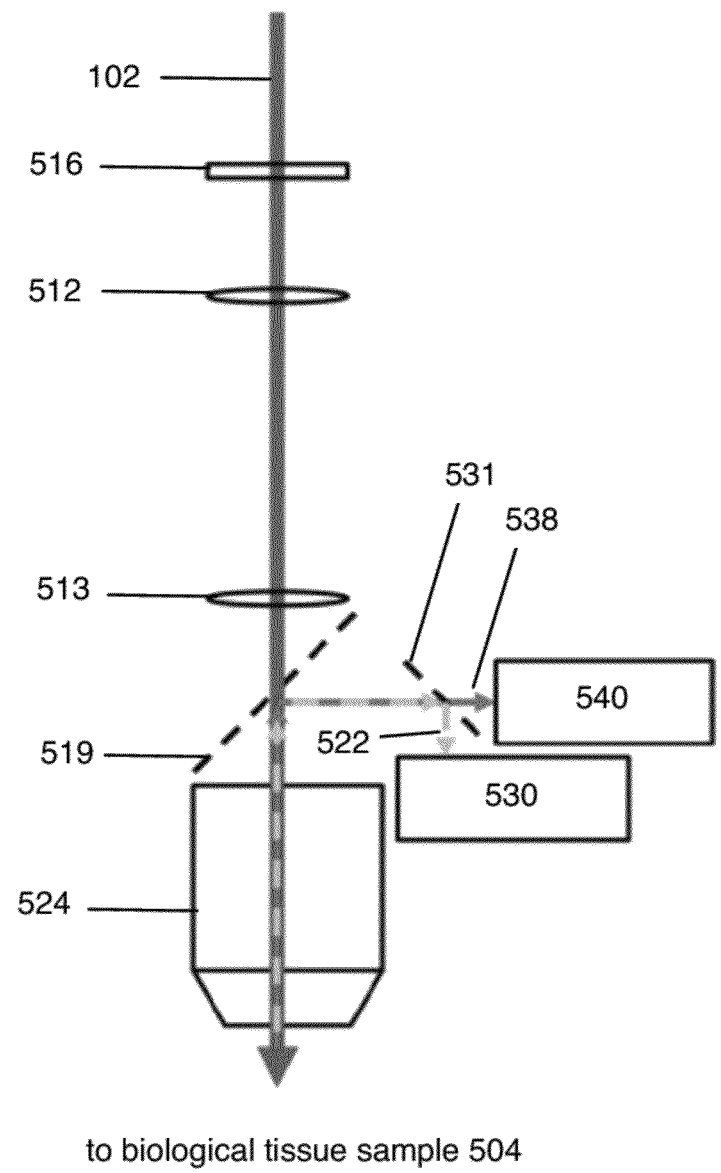
FIG. 5 shows another exemplary apparatus that includes a relay lens pair and a beam splitter.

Referring to FIG. 5, an exemplary third scheme is shown for an apparatus 500, which includes the relay lens pair 512, 513 and the beam splitter 519 that image the optical beam 102 onto the objective 524. The apparatus 500 includes a second beam splitter 531 that separates the imaging signal 538 (which is directed toward the imaging detector 540) from an intrinsic non-linear signal 522 that is produced at the biological tissue sample 504 and directs the intrinsic non-linear signal 522 toward the power detector 530. For example, the imaging signal 538 can be a multi-photon fluorescence signal and the intrinsic non-linear signal 522 can be a red or blue shifted signal due to self-phase modulation.

Figure 6:
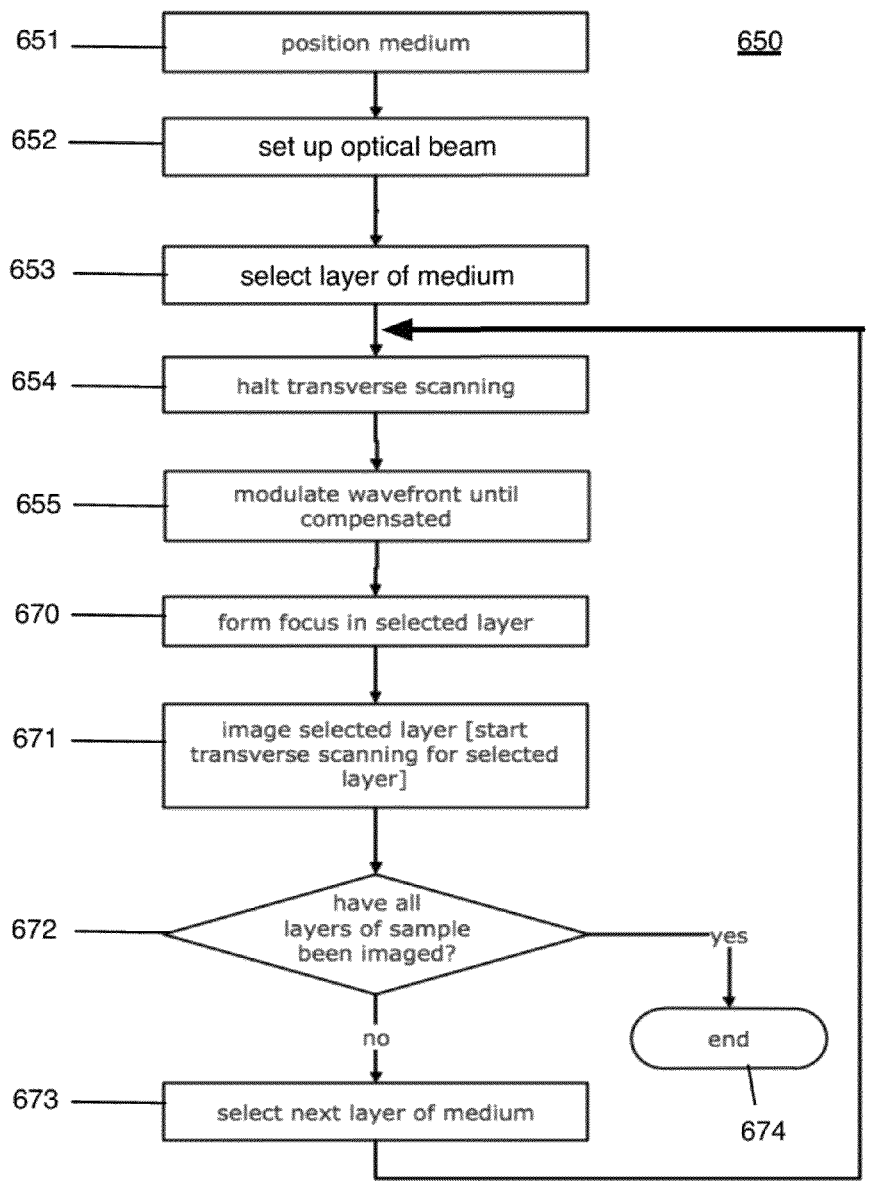
FIG. 6 shows an exemplary procedure for wavefront correction and imaging.

Referring to FIG. 6, the apparatus 100 performs a procedure 600 for wavefront correction and imaging. The random scattering medium 104 (which can be a biological tissue sample) is positioned within the apparatus 100 for imaging (step 651). The control system 132 begins the imaging by sending a signal to the light source 154 and the optical system 144 to produce the optical beam 102 and direct the optical beam 102 toward the medium 104 (step 652). Next, a first layer of the medium 104 to image is selected through control of the control system 132 (step 652). Thus, at this step, for example, the control system 232 can send a signal to the actuator 236 to position the objective 224 at a particular Z location that produces a focus 205 at the selected layer of the medium 204.

Before imaging of the medium 104 can be performed on the selected layer, the wavefront of the optical beam 102 impinging upon the medium 104 is corrected because the optical beam 102 is distorted by optical aberrations due to travel through components such as lenses and the objective 124 of the apparatus 100 or by random scattering within the medium 104. In order to correct the wavefront of the optical beam 102, all transverse scanning that could be performed by the transverse scanning optical system 144 is halted (step 654). For example, the control system 132 can send a signal to the actuators within the transverse scanning optical system 144 to halt movement of the scanning mirrors.

Once the transverse scanning is halted (step 654), the control system 132 performs wavefront modulation and compensation of the optical beam 102 until the wavefront distortions of the optical beam 102 are reduced to within an acceptable range (step 655). At this moment, a diffraction-limited focus can be formed inside the medium 104 without the need for a point guide star (step 656). Details about the procedure for step 655 are discussed below with respect to FIGS. 7 and 8.

Once the wavefront distortions are reduced to within an acceptable range (step 655), and the focus is formed (step 656), the control system 132 images the layer that was selected in step 652 by sending a signal to the transverse scanning optical system 144 to scan the optical beam 102 along the X, Y plane that is perpendicular to the Z direction of the optical beam 102 at the selected layer (step 671). The control system 132 or an operator of the apparatus 100 determines whether all of the layers of the medium 104 have been imaged (step 672), and if it is determined that they have all been imaged at step 672, then the procedure 600 ends (step 674). If it is determined that some layers of the medium 104 have not yet been imaged (step 672), then the control system 132 or the operator selects the next layer of the medium 104 for imaging (step 673) and repeats steps 654-672 until the end (step 674). The next layer of the medium 104 can be selected by the control system 132 by sending a signal to the actuator 236 to translate the objective 224 along the Z direction to thereby move the focus 205 to the next layer.

Figures 7, 8:
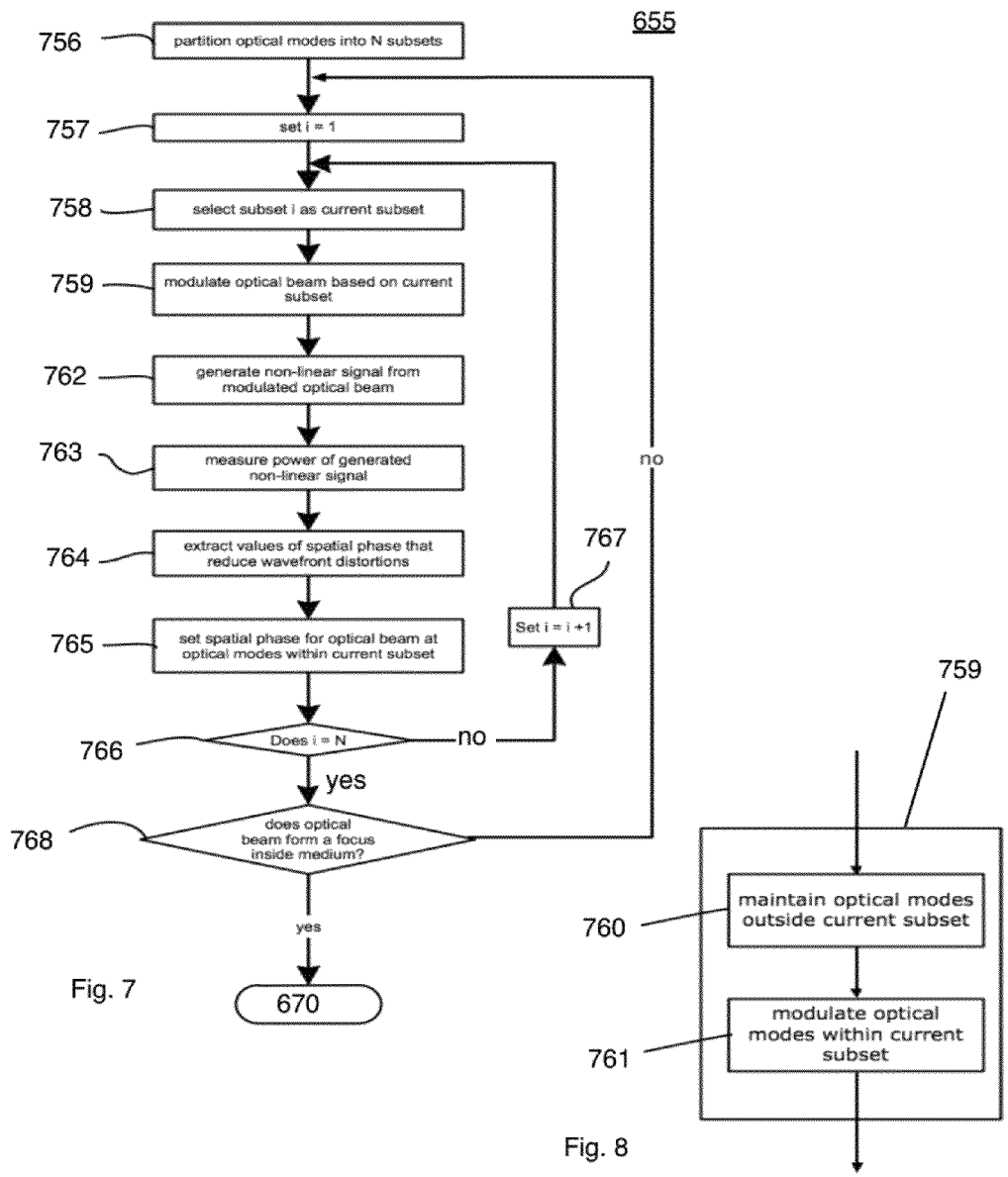
FIG. 7 shows an exemplary procedure for wavefront modulation and compensation of an optical beam.
FIG. 8 shows an exemplary procedure for modulating an optical beam.

Referring to FIG. 7, a procedure 655 is performed for wavefront modulation and compensation of the optical beam 102. Initially, the transverse optical modes of the optical beam 102 are partitioned into a plurality of N subsets of transverse optical modes (step 756). The partitioning step can be an automatic process performed by or through the control system 132, or it can be a manual process entered by an operator of the control system 132. In any case, the number N of subsets of transverse optical modes is selected based on the arrangement of the phase elements in the wavefront correction device 116. Thus, for example, if the wavefront correction device 116 includes 32×32 phase elements, then these elements can be divided into two (N=2) transverse optical mode subsets, with each subset including 512 phase elements.

Next, a first (i=1) transverse optical mode subset is selected from the partition (step 757) and that selected subset is designated as the current subset (step 758). The optical beam 102 is modulated based on the current subset (step 759). The modulation of the optical beam 102 is effected by the wavefront correction device 116, which is under control of the control system 132. As shown in FIG. 8, the modulation of the optical beam (step 759) includes maintaining those transverse optical modes of the optical beam 102 outside the current subset constant (step 760) and modulating the transverse optical modes of the optical beam 102 within the current subset (step 761). Basically, in step 761, the current subset of phase elements of the wavefront correction device 116 are modulated, while in step 760, all the other phase elements of the wavefront correction device 116 are kept stationary. In the example provided above, for the wavefront correction device 116 that includes 32×32 phase elements, a first half (512) of the phase elements are modulated simultaneously with each phase element at a unique frequency while the second half (512) of the phase elements are kept stationary.

The modulated optical beam 102 is directed through the non-linear optical system 120, which generates the non-linear optical signal 122 (step 762) due to the interaction of the optical beam 102 with the medium 104. For example, in the apparatus 200 of FIG. 2, the multi-photon fluorescence is generated.

Next, the non-linear optical signal 122 is directed to the power detector 130, which measures the power of the generated non-linear signal 122 (step 763). In some implementations, the power of the non-linear optical signal 122 is measured (step 763) by Fourier transforming the measured power.

Based on the measured power, values of the spatial phase for the optical beam 102 at transverse optical modes within the current subset are extracted, the values extracted being those that reduce the wavefront distortions in the optical beam (step 764). If the measured power is Fourier transformed at step 763, then the values can be extracted from corresponding modulation frequencies. Next, the spatial phases for the optical beam 102 are set for the optical modes within the current subset (step 765) based on the extracted values (step 764). For example, in step 765, the phases can be sign reversed before being applied to the modulated phase elements of the wavefront correction device 116.

Once the spatial phases are set (step 765), the procedure 655 determined if the selected subset (step 758) is the last subset of the partition (step 766). If it is not, then the next subset of transverse optical modes is selected from the partition by iteration (i=i+1) (step 767) and that selected subset is designated as the current subset (step 758). Thus, the steps 758-766 are performed iteratively until it is determined at step 766 that the selected subset is the last subset of the partition. In this case, each transverse optical mode subset of the entire partition will have been phase modulated.

Next, it is determined if the wavefront distortions have been reduced to within an acceptable level (step 768), for example, whether the optical beam 102 forms a diffraction-limited focus inside the medium 104 without the need for a point guide star. It is possible that this condition is met after only one pass through each transverse optical mode subset of the partition. But, more passes may be needed, depending on the number of partitions, the number of phase elements of the wavefront correction device 116, or the wavefront distortions present in the optical beam 102.

If it is determined that the wavefront distortions have not been reduced to within an acceptable level (step 768), then the steps 757-767 are repeated until it is determined at step 768 that the wavefront distortions have been reduced to within the acceptable level. At this point, the procedure 655 is completed, and imaging of the selected layer can begin (step 671).

The wavefront compensation and focus formation procedure described above can be explained as nonlinearity assisted iterative optical phase conjugation. For example, for a wavefront correction device 116 having a 32×32 array, during the parallel phase modulation at step 759, the E field ($E_i$) controlled by each of the 512 modulated elements interferes with the reference E field ($E_r$) controlled by the 512 stationary phase elements. For a single point source (guide star), the signal is strongest when $E_i$ and $E_r$ are in phase at the guide star location. Through steps 759-765, the correct phase value that makes $E_i$ and $E_r$ in phase can be determined and the newly measured 512 phase elements are ready to perform a phase conjugation and focus the optical beam 102 onto the guide star.

If multiple guide stars are present, the phase conjugation beam focuses onto multiple locations with stronger guide stars receiving stronger illumination. In the next iterative steps (at which the other 512 phase elements are selected as the current subset), the phase conjugation beam serves as the reference field to determine the phase profile for the other 512 phase elements. Different from the previous iteration, the new reference field now preferentially illuminates stronger guide stars, further increasing the signal contribution from these stronger guide stars. If the two groups of phase elements take turns serving as the reference field and to be measured iteratively as described above, eventually a focus is formed onto the strongest guide star. For linear signals, such a scheme would fail to form a focus if the target is uniform and occupies a large volume, for example, a laser beam focused inside a cell filled with fluorescence dye. However, if the signal generation involves a higher order (non-linear) process such as two-photon fluorescence (TPF) or second harmonic generation (SHG), the nonlinearity can assist the formation of a single focus. Essentially, the entire process of phase modulation and compensation is to improve or optimize the excitation wavefront to improve or maximize the generated signals. If the beam is immersed in a large and uniform target, the phase only modulation cannot cause any variation of the total signal given that the signal is generated through a linear process. However, nonlinearity favors the formation of a focus because the overall signal is stronger if a single focus is formed inside the sample 104.

Simulations of the apparatuses described above were performed using the procedure 650; the results of these simulations are shown in exemplary graphs that are included as FIGS. 9A-12C.

Figures 9A, 9B, 9C:
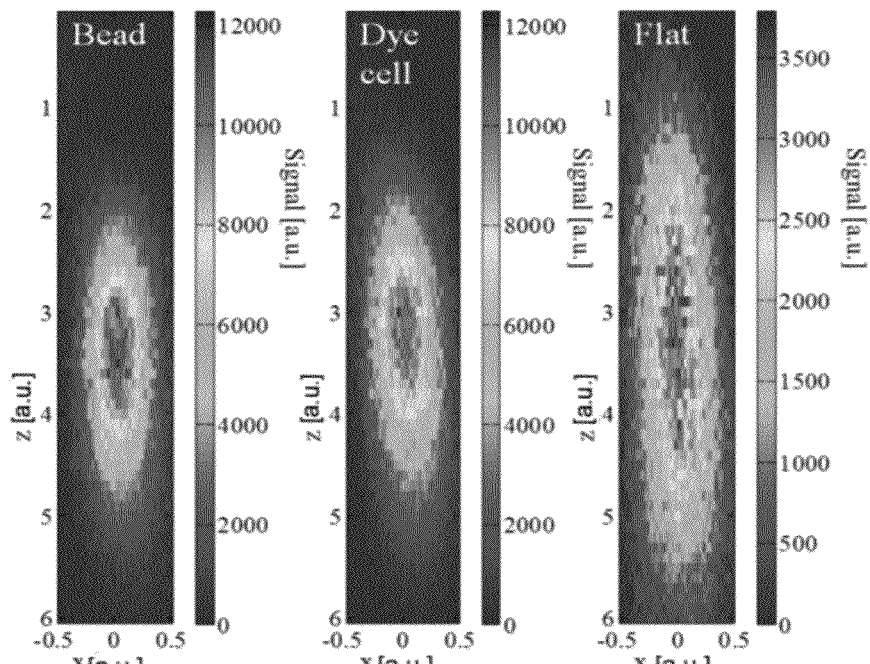
FIGS. 9A-9C show cross-sections of exemplary measured point spread functions (PSFs)
Figure 9D:
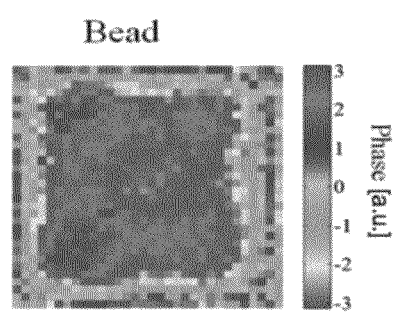
FIGS. 9D and 9E show exemplary compensation profiles.
Figure 9E:
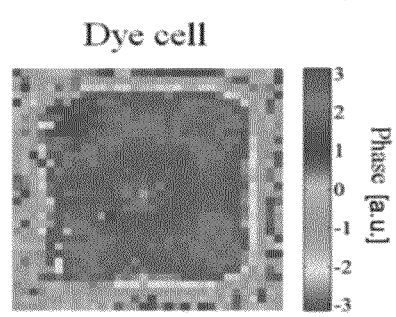

FIGS. 9A-9C show measured cross-sections of a point spread function (PSF). Each of the images shown in FIG. 9A-9C are shown in the XZ plane. However, the cross-section of the PSF in the YZ plane would be similar to that in the XZ plane. FIG. 9A shows a PSF with the compensation profile determined with beads, FIG. 9B shows a PSF with the compensation profile determined with a dye cell, and FIG. 9C shows the PSF with a flat phase, that is, with no compensation. For the example shown in FIG. 9A, the beads were 0.1 μm diameter florescence beads under a cover glass. For the example shown in FIG. 9B, the dye cell was a cell filed with fluorescence dye. The PSFs shown in FIGS. 9A-9C suggest that the techniques discussed above can utilize large volume uniform targets to form a focus. FIG. 9D shows the compensation profile determined with beads, and FIG. 9E shows the compensation profile determined with the dye cell. The images shown in FIGS. 9D and 9E represent the phase values of the elements of a MEMS mirror used as the wavefront correction device.

FIG. 10A shows a compensation profile determined through a brain tissue slice, FIG. 10B shows an example of two-photon fluorescence (TPF) imaging through brain tissue with full correction, and FIG. 10C shows TPF imaging through brain tissue with system correction. The system correction is a correction that is derived from the output of the imaging system when there is no sample for imaging present. In other words, the system correction addresses aberration caused by the optical setup itself, without a sample present.

FIG. 10D shows a compensation profile determined through mouse skull, FIG. 10E shows a TPF imaging through mouse skull with full correction, and FIG. 10F shows TPF imaging through mouse skull with system correction.

FIG. 11A shows the maximum intensity projection of GFP expressing layer 5 neurons acquired with conventional multiphoton microscopy (MPM). FIGS. 11B, 11C, and 11D show compensation profiles determined at 200, 300, and 400 μm depth, respectively. The 200, 300, and 400 μm depths may be considered to be different layers within the sample that is imaged (in this case, the neurons). Thus, the compensation profiles shown in FIGS. 11B-D are compensation profiles measured at three different layers within the sample.

FIGS. 11E, 11F, and 11G show TPF images of dendrites with full correction at corresponding depth, respectively. FIGS. 11H, 11I, and 11J show TPF images of dendrites with system correction. FIG. 11K shows image intensity as a function of depth with full correction and system correction.

Figures 12A, 12B, 12C:
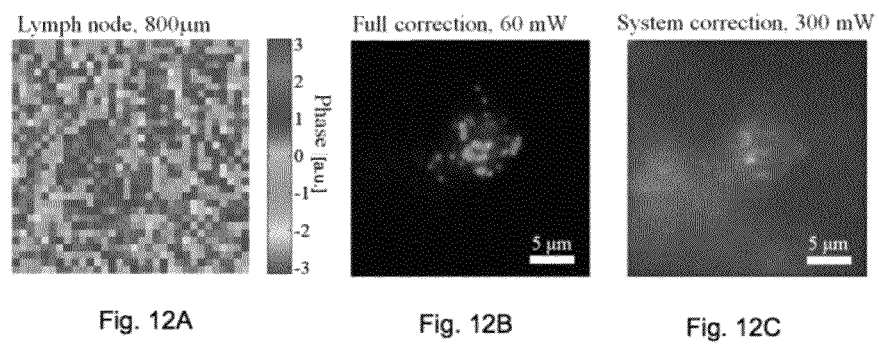
FIG. 12A shows an exemplary compensation profile determined inside a lymph node.
FIG. 12B shows a volume view of exemplary image stacks acquired with full correction.
FIG. 12C shows a volume view of exemplary image stacks acquired with system correction.

FIG. 12A shows a compensation profile determined inside of a lymph node at 800 μm in depth. FIG. 12B shows a volume view of an image stack acquired at 800 μm in depth with full correction and 60 mW excitation power. The image stack is a stack or collection of images taken at different depths or layers within the sample. FIG. 12C shows a volume view of the image stacks acquired at 800 μm depth with system correction and 300 mW excitation power.

Other implementations are within the scope of the following claims.

What is claimed is:

1. A method for measuring wavefront distortions of an optical beam directed inside a random scattering medium, the method comprising:
    partitioning transverse optical modes of the optical beam into a plurality of subsets of transverse optical modes;
    selecting one of the subsets of transverse optical modes as a current subset;
    modulating the optical beam based on the current subset by:
        maintaining the transverse optical modes of the optical beam that are outside the current subset stable; and
        modulating the transverse optical modes of the optical beam within the current subset;
    generating a non-linear optical signal from the modulated optical beam by directing the modulated optical beam through a non-linear optical system that includes the random scattering medium;
    measuring a power of the generated non-linear optical signal; and
    based on the measured power, extracting values of a spatial phase for the optical beam at transverse optical modes within the current subset, the values extracted being those that reduce the wavefront distortions in the optical beam.

2. The method of claim 1, further comprising setting the spatial phase for the optical beam at transverse optical modes within the current subset based on the extracted values of the spatial phase that reduce the wavefront distortions in the optical beam.

3. The method of claim 2, further comprising:
    after setting the spatial phase for the optical beam at optical modes within the current subset, determining if any of the optical modes of the partition have not yet been selected as the current subset;
    if a particular subset of transverse optical modes from the partition has not yet been selected as the current subset, then selecting the particular subset of transverse optical modes as the current subset;
    modulating the optical beam based on the current subset;
    generating the non-linear optical signal from the modulated optical beam by directing the modulated optical beam through the non-linear optical system;
    measuring the power of the generated non-linear optical signal; and
    based on the measured power, extracting values of the spatial phase for the optical beam at optical modes within the current subset, the values extracted being those that reduce the wavefront distortion in the optical beam.

4. The method of claim 3, further comprising setting the spatial phase for the optical beam at optical modes within the current subset based on the extracted vales of the spatial phase that reduce the wavefront distortion in the optical beam.

5. The method of claim 2, further comprising:
    determining whether the wavefront distortion has been reduced to within an acceptable range.

6. The method of claim 5, wherein the wavefront distortion is reduced to within the acceptable range if the optical beam forms a diffraction-limited focus inside the random scattering medium without the need for a point guide star.

7. The method of claim 5, wherein once it is determined that the wavefront distortion has been reduced to within an acceptable range, then causing all of the optical modes of the optical beam to be constant, scanning the optical beam along a transverse plane as the optical beam travels inside the random scattering medium, and imaging the random scattering medium.

8. The method of claim 1, wherein directing the modulated optical beam through the non-linear optical system comprises directing the modulated optical beam through the random scattering medium.

9. The method of claim 8, wherein:
generating the non-linear optical signal comprises generating a second harmonic generation of the modulated optical beam by passing the modulated optical beam through the random scattering medium; and
measuring the power of the generated non-linear optical signal comprises measuring the power of the second harmonic generation.

10. The method of claim 1, wherein directing the modulated optical beam through the non-linear optical system comprises directing the modulated optical beam through a multi-photon fluorescence microscope toward a biological sample.

11. The method of claim 10, wherein:
generating the non-linear optical signal from the modulated optical beam comprises generating multi-photon fluorescence from the biological sample due to a multi-photon interaction of the modulated optical beam with the biological sample; and
measuring the power of the generated non-linear optical signal comprises measuring the power of the multi-photon fluorescence.

12. The method of claim 1, wherein:
measuring the power of the generated non-linear optical signal comprises Fourier transforming the measured power; and
extracting values of the spatial phase for the optical beam at optical modes within the current subset comprises extracting the values of the spatial phase from the Fourier transformed data.

13. The method of claim 1, wherein extracting the values comprises extracting the values without analyzing the spectrum of the generated non-linear optical signal.

14. The method of claim 1, wherein modulating the optical modes of the optical beam within the current subset comprises modulating each optical mode within the current subset at a distinct frequency.

15. The method of claim 1, wherein partitioning the optical modes into a plurality of subsets of transverse optical modes comprises partitioning the transverse optical modes into at least three subsets of transverse optical modes.

16. An apparatus for measuring wavefront distortions of an optical beam directed inside a random scattering medium, the apparatus comprising:
a wavefront correction device having a spatial phase profile on its surface and configured to:
receive the optical beam; and
output a modulated optical beam;
a non-linear optical system that receives the modulated optical beam output from the wavefront correction device and is configured to generate a non-linear optical signal from the modulated optical beam;
a power detector configured to detect a power of the generated non-linear optical signal; and
a control system connected to the wavefront correction device and to the power detector, and configured to:
partition transverse optical modes of the optical beam into a plurality of subsets of transverse optical modes;
select a transverse optical mode subset from the partition as a current subset;
output a signal to the wavefront correction device to cause it to modulate the optical beam by modulating the transverse optical modes of the optical beam within the current subset and by keeping the transverse optical modes of the optical beam outside the current subset constant;
receive the detected power from the power detector; and
based on the measured power, extract values of a spatial phase for the optical beam at transverse optical modes within the current subset, the values extracted being those that reduce the wavefront distortions in the optical beam.

17. The apparatus of claim 16, wherein the control system is configured to set the spatial phase for the optical beam at transverse optical modes within the current subset based on the extracted values of the spatial phase that reduce the wavefront distortions in the optical beam.

18. The apparatus of claim 16, further comprising an objective that directs the optical beam toward and into the random scattering medium.

19. The apparatus of claim 16, wherein the generated non-linear optical signal comprises the second harmonic generation signal generated from the interaction of the optical beam with the random scattering medium.

20. The apparatus of claim 16, wherein the non-linear optical system comprises a multi-photon fluorescence microscope and the random scattering medium comprises a biological tissue sample.

21. The apparatus of claim 20, wherein the generated non-linear optical signal comprises the multi-photon fluorescence output from the biological tissue sample due to a multi-photon interaction of the modulated optical beam with the biological tissue sample.

22. A method for measuring wavefront distortions of an optical beam directed inside a random scattering medium, the method comprising:
partitioning transverse optical modes of the optical beam into a plurality of subsets of transverse optical modes;
for each transverse optical mode subset of the partition:
A. selecting one of the transverse optical mode subsets as a current subset;
B. modulating the optical beam based on the current subset by maintaining the transverse optical modes of the optical beam that are outside the current subset constant and modulating the transverse optical modes of the optical beam within the current subset;
C. generating a non-linear optical signal from the modulated optical beam by directing the modulated optical beam through a non-linear optical system that includes the random scattering medium;
D. measuring a power of the generated non-linear optical signal;
E. based on the measured power, extracting values of a spatial phase for the optical beam at transverse optical modes within the current subset, the values extracted being those that reduce the wavefront distortions in the optical beam;
F. setting the spatial phase for the optical beam at transverse optical modes within the current subset based on the extracted values of the spatial phase that reduce the wavefront distortions in the optical beam; and repeating steps A-F until the wavefront distortions of the optical beam have been reduced to an acceptable amount.

* * * * *